United States Patent [19]

Butler

[11] 4,187,311

[45] Feb. 5, 1980

[54] 3-ARYLOXY-1-CARBOALKOXYETHYL-PYRIDINIUM COMPOUNDS AND COMPOSITIONS

[75] Inventor: Donald E. Butler, Ann Arbor, Mich.

[73] Assignee: Warner-Lambert Company, Morris Plains, N.J.

[21] Appl. No.: 960,251

[22] Filed: Nov. 13, 1978

[51] Int. Cl.$^2$ ............... C07D 213/65; A61K 31/44
[52] U.S. Cl. ................... 424/263; 546/301; 546/302
[58] Field of Search ............... 546/301, 302; 424/263

[56] References Cited

PUBLICATIONS

Thorne et al. "Chem. Abstracts", vol. 80, (1974), No. 14854v.

Primary Examiner—Alan L. Rotman
Assistant Examiner—R. W. Ramsuer
Attorney, Agent, or Firm—Stephen Raines; David B. Ehrlinger; Frank S. Chow

[57] ABSTRACT

3-Aryloxy-1-carboalkoxyethylpyridinium compounds, which are useful as pharmacological agents, especially as agents for the treatment of senility and reversal of amnesia, are disclosed. The compounds can be produced by reacting 3-aryloxypyridine with an alkyl acetate containing a displaceable group.

9 Claims, No Drawings

3-ARYLOXY-1-CARBOALKOXYETHYL-PYRIDINIUM COMPOUNDS AND COMPOSITIONS

SUMMARY AND DETAILED DESCRIPTION

The present invention relates to new 3-aryloxy-1-carboalkoxyethylpyridinium compounds. More particularly, the invention relates to new 3-aryloxy-1-carboalkoxyethylpyridinium compounds of the formula

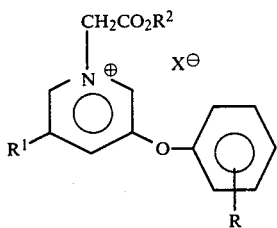

and to a method for the production of the foregoing compounds; where R is hydrogen, fluorine or chlorine; $R^1$ is hydrogen or lower alkyl, $R^2$ is lower alkyl and X is a pharmaceutically-acceptable anion.

The preferred compounds are those wherein R is hydrogen and fluorine; $R^1$ is hydrogen or methyl, $R^2$ is ethyl and X is bromine.

The term "lower alkyl" is intended to mean an alkyl group of from one to four carbon atoms, such as methyl, ethyl, t-butyl, etc.

The term "pharmaceutically-acceptable anion" is intended to mean a relatively non-toxic anion, such as the chloride, fluoride, sulfate [two equivalents of pyridinium compound would be coupled to a sulfate moiety], acetate, benzoate, etc.

In accordance with the invention, the foregoing compounds of formula I can be prepared by reacting a compound of the formula

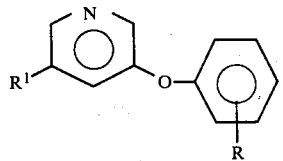

with a compound of the formula

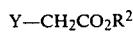

wherein R, $R^1$ and $R^2$ are as previously defined and Y is a standard leaving group, such as halogen, tosylate, benzenesulfonate, etc., preferably chlorine or bromine. The compounds where X is as previously defined are formed when Y when disassociated from Y—$CH_2$—$CO_2R^2$ yields an anion X or yields an anion that may be readily converted to X via routine laboratory methods, such as the use of an ion exchange method.

Although excess quantities of either reactant may be used, it is preferred to employ equimolar amounts of reactants.

The reaction may be carried out in most any organic solvent, which would include; lower alkylnitriles, such as acetonitrile; lower alcohols such as ethanol, n-butanol; hydrocarbons such as benzene, toluene and xylene; ethers such as dioxane and diethylene glycol dimethyl ether; dimethyl sulfoxide; N-methyl-pyrrolidone and N-methylpiperidone and mixtures of these. The preferred solvent is acetonitrile.

The reaction is carried out at a temperature range of 0° to 110° C. for periods of from one to 24 hrs, preferably 70° to 90° C. for from 8 to 16 hrs.

The product may be isolated by evaporation of the solvent until crystallization occurs. The anion may be exchanged for a different anion using an anion exchange resin.

While most of the starting materials are known compounds and the remainder are prepared by standard laboratory methods, the method of preparation of a number of starting materials of the formula II is shown in another part of the specification.

The compounds of the invention may exist in anhydrous form as well as in solvated, including hydrated, forms. In general, the hydrated forms and the solvated forms with pharmaceutically-acceptable solvents are equivalent to the anhydrous or unsolvated form for the purposes of the invention.

Also in accordance with the invention, pharmaceutical compositions may be produced by formulating the compounds of formula I in dosage unit form with a pharmaceutical carrier. Some examples of dosage unit forms are tablets, capsules, lozenges, and pills; as well as powders and aqueous and non-aqueous solutions and suspensions packaged in containers containing either one or some larger number of dosage units and capable of being sub-divided into individual doses by such means as measurement into teaspoon or other standard container. Some examples of suitable pharmaceutical carriers, including pharmaceutical diluents, are gelatin capsules; sugars such as lactose and sucrose; starches such as corn starch and potato starch; cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol; glycerine, sorbitol; polyethylene glycol; water; agar; alginic acid; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient in the foregoing compositions can be varied within wide limits but for practical purposes it is preferably present in a concentration of at least 10% in a solid composition and at least 2% in a primarily liquid composition. The most satisfactory compositions are those in which a much higher proportion of the active ingredient is present. The compositions of the invention preferably contain from 1 to 500 mg, preferably 5 to 100 mg of the active ingredient per dosage unit so that the entire amount to be administered during a day can be made up from a reasonable number of dosage units.

The compounds of formula I may be incorporated into formulations intended for parenteral administration. Such compositions may be in a powdered form intended to be combined with an isotonic solution containing other ingredients such as preservatives, etc. or may be initially formulated as part of an isotonic solution which may contain preservatives, other active ingredients, etc.

The compounds of the invention are new chemical compounds of value as pharmacological agents. More specifically, they are agents which are potentially useful in treating patients suffering from senility. The compounds also find use in the treatment of induced amnesia. The compounds of the invention generally would be administered to mammals in a dosage range of from about 0.014 to about 21.4 mg per kg of body weight per day, preferably 0.36 to 10.7 mg per kg per day. Thus 1 mg to 1500 mg, preferably 25 mg to 750 mg, are administered to a 70 kg host per day.

The effectiveness of the aforementioned compounds is determined by the following test. This test is designed to show the compound's ability to reverse amnesia produced by electroconvulsive shock.

One hundred male mice (Carworth, CF-1 strain, 19–21 g at time of shipment) are divided into five groups of 20 mice each. Each mouse is placed, one at a time, on a small shelf attached to the outside wall of a test box. In this position the mouse is suspended in space. Therefore, the mouse is motivated to step from the shelf through a conveniently placed small hole into the interior of the box. As soon as the mouse has all four feet within the semidarkened interior of the box, the grid floor of the box is electrified (1.5 milliamps, 3 second duration) to produce a strong pain-fear reaction from the animal. About five seconds thereafter, the mouse is removed from the test box and placed in a group holding cage.

Two hours after the above training the mice are given a single electroconvulsive shock produced by 20 milliamps delivered for 0.5 seconds through the ears. Immediately thereafter, the mice are returned to the holding cage.

Two hours after the convulsive treatment, the mice are injected intraperitoneally with the chemical being assesed. Usually three doses of the chemical will be tested at a time.

One hour after the drug treatment, the mice are tested for memory of the painful foot shock received within the self-box apparatus. This testing is accomplished by once again placing each mouse on the small shelf attached to the test box. Any mouse that stays on the shelf for 60 seconds without entering the box is counted as remembering the painful foot shock received within the box five hours earlier. Any mouse entering the box within the 60-second period is counted as having amnesia for the painful event.

Using this 60-second criterion, appropriate control experiments show (1.) 100 percent of mice will enter the box if no foot shock is delivered during the original training, (painful foot shock is necessary if the mice are to develop an aversion to entering the test box) (2.) 100 percent of mice will enter the box under the foregoing conditions even when treated with electroconvulsive shock at the three-hour point prior to testing (electroconvulsive shock treatment itself does not generate a fear of entering the test box).

The five groups of mice are treated as follows:

| Group | |
|---|---|
| 1) Ceiling Control Group: | Placebo |
| 2) Base Line Control Group: | Electroconvulsive shock, Placebo |
| 3) 1st Drug Dose Group: | Electroconvulsive shock, 1-(2-alkoxy-2-oxoethyl)-3- aryloxypyridinium halide |
| 4) 2nd Drug Dose Group: | Electroconvulsive shock, 1-(2-alkoxy-2-oxoethyl)-3- aryloxypyridinium halide |
| 5) 3rd Drug Dose Group: | Electroconvulsive shock, 1-(2-alkoxy-2-oxoethyl)-3- aryloxypyridinium halide |

The percentage of amnesia reversal is determined as follows for each drug group:

$$\text{Percent amnesia reversal} = \frac{\text{Drug group} - \text{Base line control group}}{\text{Ceiling control group} - \text{Base line control group}} \times 100$$

The following criteria is used in interpreting the percent of amnesia reversal scores:

40 percent or more (active=A) 25 to 39 percent (borderline=C) and 0 to 29 percent (inactive=N).

The duration of the electroconvulsive shock can be varied making the test more or less difficult for a compound to demonstrate an A or C rating. Thus a compound with activity in senile patients and in patients with early memory defects, Piracetam ® [Acta Psychiat. Scand. 54, 150 (1976)], has been administered in this test using the above methodology and 0.2 second and 0.5 second electroconvulsive shock and gave the following results.

| Piracetam ® (mg/kg) | 0.2 sec ECS | 0.5 sec ECS |
|---|---|---|
| 80 | C | N |
| 20 | A | N |
| 5 | C | N |

The inverted U shaped dose response curve is typical of this type of agent.

The following table reports the results for certain compounds of the invention:

Table 1

| Compound Example | LMC test Dose Compound Dose levels (mg/kg) | | | | | | | | |
|---|---|---|---|---|---|---|---|---|---|
| | 0.63 | 1.25 | 2.5 | 5.0 | 10. | 20. | 40. | 80. | 160 |
| 1 | N | A | A | A | C | A | A | A | A |
| 2 | | N | N | C | N | A | | N | |
| 3 | | N | N | C | A | N | | N | |
| 4 | | N | N | A | C | A | | C | |
| 5 | | | N | | C | | N | | |
| 6 | | N | C | N | A | | N | | |

The invention is illustrated by the following examples.

EXAMPLE 1

1-(2-ethoxy-2-oxoethyl)-3-phenoxypyridinium bromide

To a solution of 17.1 g of 3-phenoxypyridine [J. Amer. Chem. Soc 59, 297 (1937)] in 100 ml of acetonitrile is added 16.7 g of ethyl bromoacetate and the solution is refluxed for 8 hours. The resulting mixture is concentrated at reduced pressure and the crystalline solid is isolated by filtration to yield 1-(2-ethoxy-2-oxoethyl)-3-phenoxypyridinium bromide; mp 125°–126° C. after recrystallization from acetonitrile-diethyl ether.

EXAMPLE 2

1-(2-ethoxy-2-oxoethyl)-3-phenoxypyridinium chloride

By substituting 13 g of ethyl chloroacetate for the ethyl bromoacetate in Example 1, the product is 1-(2-ethoxy-2-oxoethyl)-3-phenoxypyridinium chloride; mp 119°–121° C.

EXAMPLE 3

1-(2-ethoxy-2-oxoethyl)-3-(2-fluorophenoxy)-pyridinium bromide

To a solution of 1 g of 3-(2-fluorophenoxy) pyridine in 40 ml of acetonitrile is added 0.9 g of ethyl bromoacetate and the solution is refluxed 16 hours. The solvent is removed in vacuo to yield 1-(2-ethoxy-2-oxoethyl)-3-(2-fluorophenoxy) pyridinium bromide; mp 133°–135° C.

EXAMPLE 4

1-(2-methoxy-2-oxoethyl)-3-phenoxypyridinium bromide

By substituting 16 g of methyl bromoacetate for the ethylbromoacetate in Example 1, the product is 1-(2-methoxy-2-oxoethyl)-3-phenoxypyridinium bromide; mp 137°–139° C. after recrystallization from ethanol-diethyl ether.

EXAMPLE 5

1-(2-ethoxy-2-oxoethyl)-3-methyl-5-phenoxypyridinium bromide

By substituting 17.3 g of 5-methyl-3-phenoxypyridine for the 3-phenoxypyridine in Example 1, the product is 1-(2-ethoxy-2-oxoethyl)-3-methyl-5-phenoxypyridinium bromide; mp 145°–147° C.

EXAMPLE 6

Pharmaceutical Composition containing 1-(2-Ethoxy-2-oxoethyl)-3-phenoxypyridinium bromide

| Ingredient | Quantity |
| --- | --- |
| 1-(2-Ethoxy-2-oxoethyl)-3-phenoxypyridinium bromide | 150 g |
| Lactose | 1038 g |
| Corn Starch | 39 g |
| Hydroxypropyl cellulose | 30 g |
| Magnesium stearate | 7 g |
| Ethanol-water 50:50 | qs |

The 1-(2-ethoxy-2-oxoethyl)-3-phenoxypyridinium bromide, lactose and hydroxypropyl cellulose are blended and granulated with 50:50 ethanol-water. The wet granulation is screened, dried and re-screened. The resulting dried granulation is blended with the magnesium stearate and the corn starch, and the mixture is compressed into 225 mg tablets using 11/32 inch standard concave punches. Yield equals approximately 6,000 tablets each containing 25 mg of 1-(2-ethoxy-2-oxoethyl)-3-phenoxypyridinium bromide.

INTERMEDIATE TO EXAMPLE 3

3-(o-fluorophenoxy)pyridine

A solution of 100 g of o-fluorophenol in 50 ml of toluene is added to a suspension of 102 g of potassium t-butoxide in 400 ml of toluene. The mixture is concentrated at reduced pressure and 141 g of 3-bromopyridine plus 0.5 g of finely divided copper powder is added. The non-homogeneous mixture is heated to 165° C. by distillation of 20 ml of a low boiling liquid and held between 165° C. and 180° C. for 2 hours. The mixture is cooled, 700 ml of toluene is added and the mixture is filtered to remove inorganic salts. The organic layer is treated with an excess of 10% perchloric acid solution and the aqueous phase is separated. The aqueous phase is made strongly basic with excess 50% sodium hydroxide solution and extracted 3 times with 300 ml portions of toluene. The toluene extracts are combined, dried by distillation at atmospheric pressure and distilled to yield 3-(o-fluorophenoxy)pyridine, bp 127°–137° C. at 6 mm.

INTERMEDIATE TO EXAMPLE 6

3-Methyl-5-phenoxypyridine

A solution of 100 g of phenol, 26 g of potassium tertiary butoxide in 200 ml of toluene is distilled until the temperature of the undistilled residue reaches 165° C. The solution is cooled to 155° C. and 25 g of 5-bromo-3-methylpyridine [Rec. Trav. Chim., 84, 951–64 (1965)] is added along with 100 mg of copperbronze powder. The mixture is stirred and refluxed for 16 hours. The mixture is cooled and diluted with 250 ml of toluene. The solution is filtered through filter aid and treated with a large excess of 50% sodium hydroxide. The toluene solution is concentrated at reduced pressure and the 3-methyl-5-phenoxypyridine isolated by distillation; bp 150°–152° C. at 18 mm.

I claim:

1. A compound of the formula

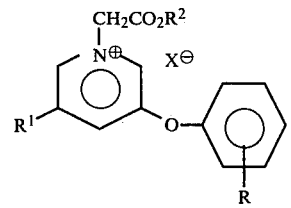

where R is hydrogen, fluorine or chlorine; $R^1$ is hydrogen or lower alkyl, $R^2$ is lower alkyl and $X^\ominus$ is a pharmaceutically-acceptable anion.

2. The compounds of claim 1 wherein R is hydrogen and fluorine; $R^1$ is hydrogen or methyl, $R^2$ is ethyl and $X^\ominus$ is bromide.

3. The compound of claim 1 having the name 1-(2-ethoxy-2-oxoethyl)-3-phenoxypyridinium bromide.

4. The compound of claim 1 having the name 1-(2-ethoxy-2-oxoethyl)-3-phenoxypyridinium chloride.

5. The compound of claim 1 having the name 1-(2-ethoxy-2-oxoethyl)-3-(2-fluorophenoxy(pyridinium bromide.

6. The compound of claim 1 having the name 1-(2-methoxy-2-oxoethyl)-3-phenoxypyridinium bromide.

7. The compound of claim 1 having the name 1-(2-ethoxy-2-oxoethyl)-3-methyl-5-phenoxypyridinium bromide.

8. A pharmaceutical composition comprising an antisenility or induced amnesia reversing effective amount of a compound of claim 1 and a pharmaceutical carrier.

9. A method for treating senility or induced amnesia which comprises administering an effective amount of a composition of claim 8.

* * * * *